United States Patent

Gregor et al.

Patent Number: 5,811,665
Date of Patent: Sep. 22, 1998

[54] LARGE SCALE SORPTION-DRIVEN SOLID STATE CHROMATOGRAPHY

[75] Inventors: Vlad E. Gregor, Del Mar; Scott Schreckengaust, San Diego, both of Calif.

[73] Assignee: Alanex Corporation, San Diego, Calif.

[21] Appl. No.: 712,145

[22] Filed: Sep. 11, 1996

[51] Int. Cl.⁶ .................................................. G01N 30/60
[52] U.S. Cl. ...................... 73/61.53; 210/656; 210/198.2; 422/70
[58] Field of Search ................................ 73/61.52, 61.53; 210/656, 198.2; 422/70; 436/161

[56] References Cited

U.S. PATENT DOCUMENTS

| | | |
|---|---|---|
| 3,387,710 | 6/1968 | Pogacar . |
| 3,465,884 | 9/1969 | Matherne . |
| 3,600,306 | 8/1971 | Tocci . |
| 3,839,205 | 10/1974 | Okumura et al. . |
| 4,261,835 | 4/1981 | Creeger . |
| 4,348,286 | 9/1982 | Felton . |
| 4,587,020 | 5/1986 | Nakagawa et al. . |
| 4,743,373 | 5/1988 | Rai et al. . |
| 4,828,704 | 5/1989 | Yamamoto . |
| 4,906,378 | 3/1990 | Hagen et al. . |
| 5,484,532 | 1/1996 | Rice . |

OTHER PUBLICATIONS

Fodor et al., *Science* 251:767–773, (1991), "Light–Directed, Spatially Adressable Parallel Chemical Synthesis".

*Primary Examiner*—Michael Brock
*Attorney, Agent, or Firm*—Knobbe, Martens, Olson and Bear

[57] ABSTRACT

A system for preparative sorption driven chromatographic separation of organic compounds comprising a chromatographic element having a focusing zone in a porous tip with a vertex having a first diameter for receiving sample and solvent and a base having a wider second diameter, and an elongated resolving zone of at least the second diameter is disclosed. The system may further include a porous solvent transfer block for transferring solvent from a source to the tip. A method of chromatographically isolating an organic compound using the system is disclosed.

26 Claims, 2 Drawing Sheets

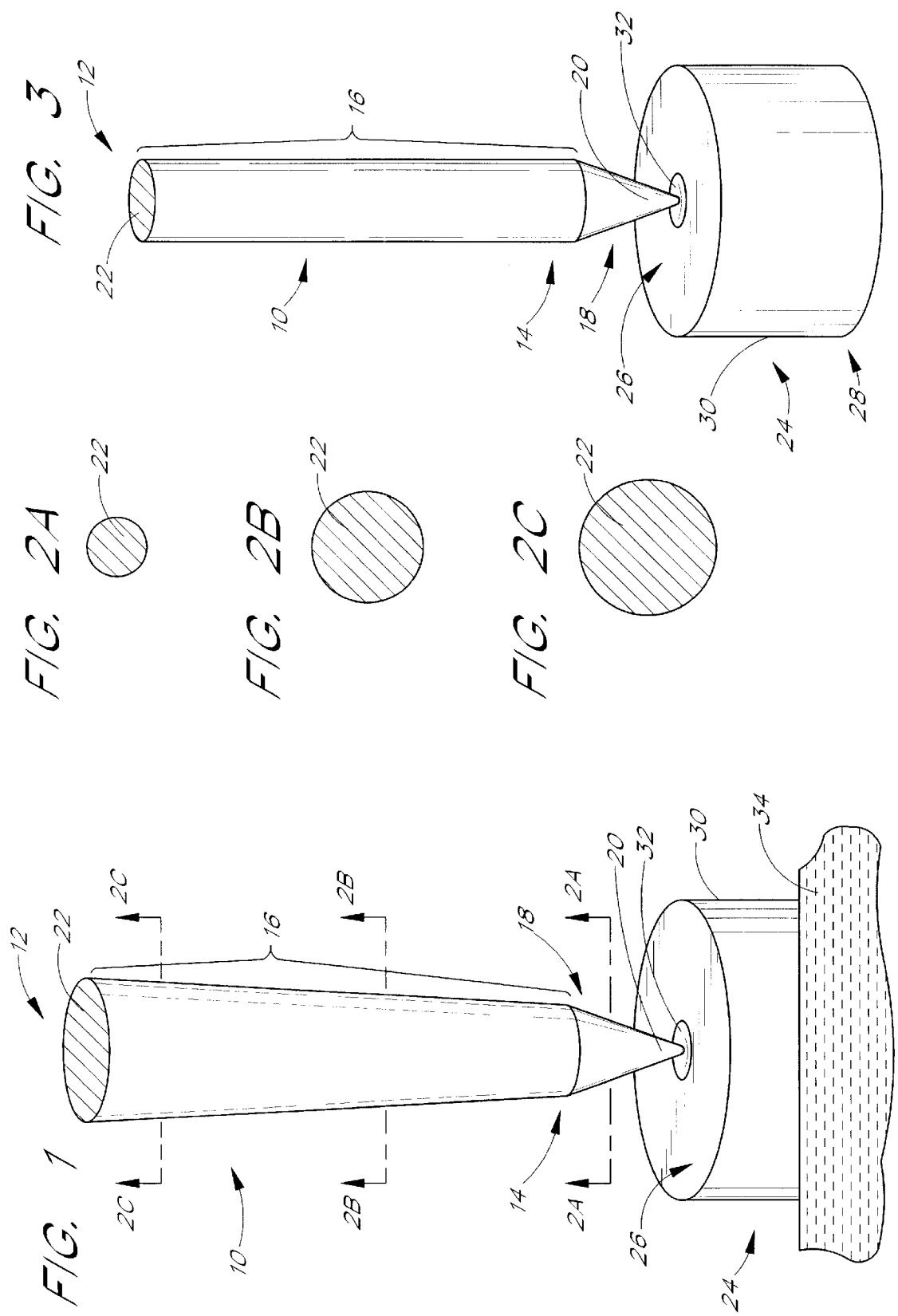

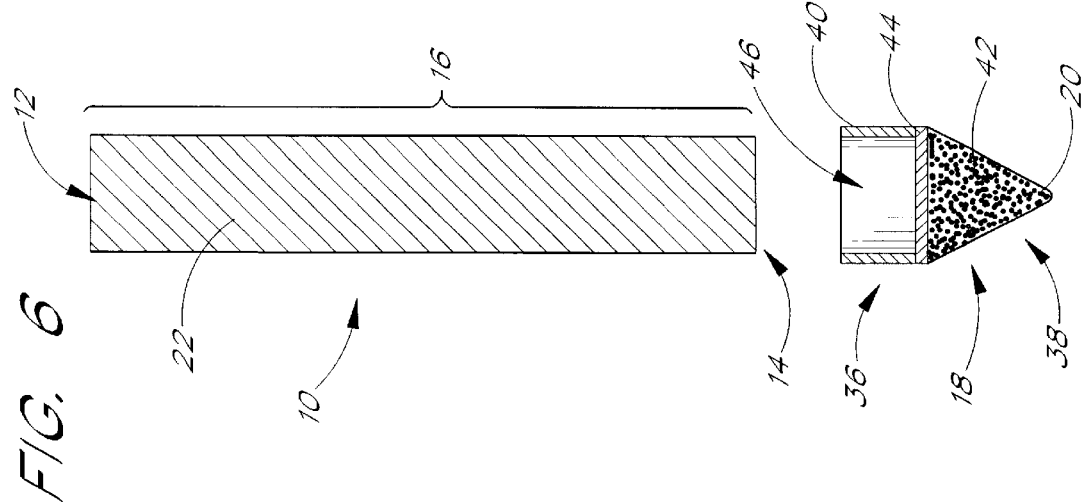
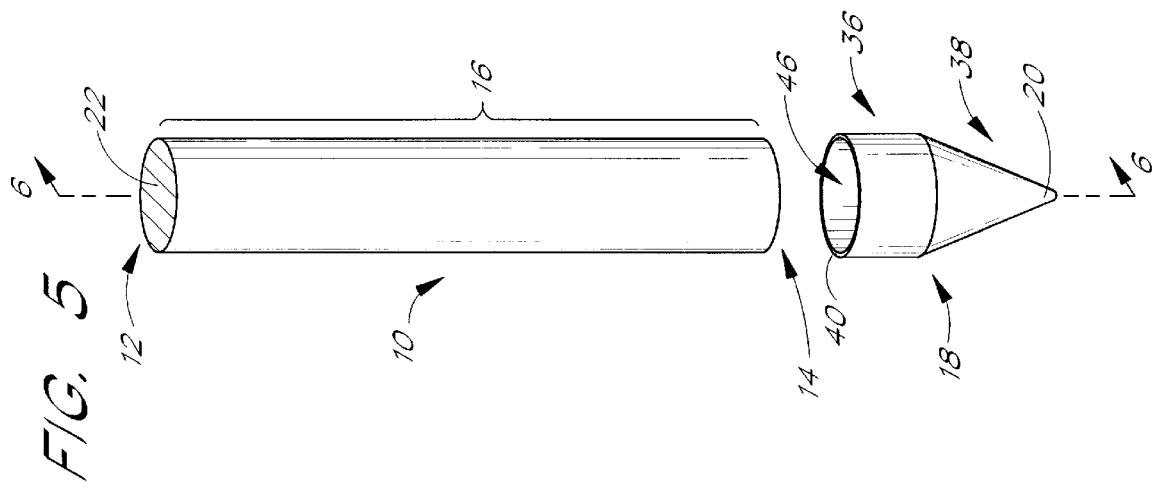
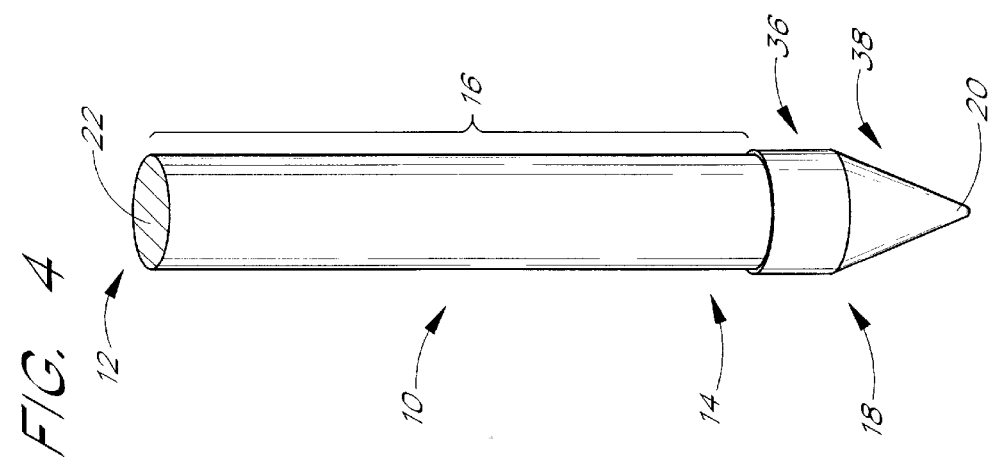

ly useful compounds for industrial and medical applications. This invention discloses an improved chromatographic device and methods of preparative scale chromatographic separation of organic compounds in a mixture.

LARGE SCALE SORPTION-DRIVEN SOLID STATE CHROMATOGRAPHY

BACKGROUND OF THE INVENTION

1. Field of the Invention

This invention relates to a chromatographic separation of materials, and specifically relates to improved preparative chromatography of organic compounds using a self-supporting chromatographic column that concentrates a compound into a narrow band during movement of the compound through the column from a narrower focusing zone to a wider resolution zone.

2. Description of the Relevant Art

Chromatography generally refers to a variety of processes for isolating components of a sample mixture by applying a sample to a stationary phase and then separating the components by applying a mobile phase (gas or liquid) which causes the components to pass through the stationary phase at different rates. The rate a compound moves through the stationary phase compared to the mobile phase (expressed as the ratio $R_f$) is determined by the affinity of the compound for the stationary phase compared to that of the mobile phase. Compounds with sufficiently different $R_f$ can be physically separated by chromatography depending on the separation conditions used. Whereas analytical chromatography is used to identify and quantitate the components in a mixture, preparative chromatography is used to isolate and purify relatively large quantities of compounds from a mixture. After preparative chromatography, generally a spot or band of a separated compound of interest is purified from the chromatographic medium using standard mechanical and/or chemical extraction techniques.

Chromatographic methods are often characterized by the solid phase and/or mobile phase used, the configuration of the solid phase, or by the resolving mechanism. Well-known chromatographic methods include column chromatography, thin layer chromatography (e.g., on a coated plate, rod, or tube), paper (or other flexible sheet support) chromatography, gas chromatography, ion exchange chromatography and affinity chromatography. Many types of devices for chromatographic separation are known including plates, rods, tubes, cones or channels coated with a chromatographic medium (e.g., as disclosed in U.S. Pat. Nos. 3,465,884, 3,387,710, 3,839,205, 4,261,835, 4,587,020 and 4,828,704). Chromatography plates in a wedge-layer configuration (U.S. Pat. No. 4,348,286) or having a constricted neck between to solvent pick-up zone and the development zone (U.S. Pat. No. 3,600,306) are known. Chromatographic devices that employ radial flow through a column or disk form are described in U.S. Pat. No. 4,743,373 and U.S. Pat. No. 5,484,532. A variety of chromatographic media are known as disclosed in the patents listed above and U.S. Pat. No. 4,906,378.

Preparative scale chromatography generally uses a relatively large layer or column of chromatographic medium attached to or contained within a rigid outer support for separation of compounds. Preparative chromatography is often time consuming and inefficient because the columns are difficult to construct and bands of compounds are difficult to separate. Because of the relatively large volumes of sample used in preparative chromatography, the initial spot or band applied to the chromatographic medium is generally large and diffuse, resulting in diffuse distribution of compounds as they move through the solid phase. Moreover bands can diffuse, spread or "trail" into one another, resulting in incomplete separation of one compound from another. Incomplete separation can result when a compound exhibits different migration rates through the chromatographic medium attached to a solid support depending on its location in the medium. That is, the compound can lag behind the front where it is near the adsorbent/air interface and can moves ahead or lag behind where it is near the adsorbent/support interface, depending on the capillary properties of the support material.

The wider the band of a compound in the chromatographic medium, the more likely that it will overlap with a band of another compound. Moreover, where compounds have very similar $R_f$, band separation becomes even more difficult. Thus, by decreasing the band widths during chromatography, separation between the bands of compounds increases, making compound purification more efficient.

In addition to problems of band resolution, preparative chromatography often requires relatively large volumes of fluid solvents, particularly if plate or thin layer chromatography is used, because the atmosphere surrounding the plate or thin layer must be saturated with solvent vapor for the solvent front to move evenly through the chromatographic medium. Because many commonly used chromatographic solvents are flammable, acidic or caustic and noxious, methods that minimize the amount of solvent needed and exposure of personnel to volatile solvents are preferred.

Preparative scale chromatography is useful for isolating compounds, particularly synthetic organic compounds, that have many uses in industry, medical diagnosis and treatment, and in food production. For example, synthetic small organic compounds such as polymers or peptidomimetics can be used to manipulate enzymatic reactions by modifying the enzyme's active site to inhibit or enhance enzymatic activity. Although analytic methods can identify potentially useful synthetic compounds (e.g., from a library made by combinatorial or parallel synthetic methods), inefficient isolation of quantities of sufficiently pure synthetic compounds often limits the use of the identified compounds. Because combinatorial synthesis (Fodor et al., *Science* 251:767–773, 1991) often produces many structurally related organic compounds of interest (e.g., derivatives of a basic core structure), efficient preparative scale chromatography is needed to isolate pure samples of each of these related compounds. Efficient methods for isolating these many compounds in sufficient purity and quantity for testing in the appropriate reaction or system is needed to provide potentially useful compounds for industrial and medical applications. This invention discloses an improved chromatographic device and methods of preparative scale chromatographic separation of organic compounds in a mixture.

SUMMARY OF THE INVENTION

According to one aspect of the invention, there is provided a preparative-scale sorption-driven chromatographic system, including a self-supporting chromatographic element, the chromatographic element being made of adsorbent material with no external support formed into an elongated shape having a first end and a second end, with a focusing zone proximate to the first end and a resolution zone that extends from the focusing zone to the second end, wherein the focusing zone tapers from a small cross section at the first end to a larger second cross section where the focusing zone meets the resolution zone, and wherein the resolution zone has a cross section that is at least as large as the second cross section. In one embodiment, the first end includes a sample application zone proximal to the focusing zone and distal to the resolution zone. In another embodiment, the focusing zone has the shape of essentially a solid cone, hemisphere, paraboloid or pyramid. In yet another embodiment, the resolution zone has a uniform circular cross-section. In one embodiment, the resolution zone has a circular cross section that progressively increases in cross section from the second cross section where the focusing zone meets the resolution zone to a larger cross section at the second end. In another embodiment, the resolution zone has a square cross-section. In a preferred embodiment, the focusing zone and the resolution zone are integrally connected, whereas in another preferred embodiment the focusing zone and the resolution zone are releasably attachable separate zones. In one embodiment, the chromatographic system further includes a porous solvent transfer block. In a preferred embodiment, the solvent transfer block is a fritted material having a depression for receiving the first end of the chromatographic element. In a preferred embodiment, the adsorbent material is silica gel, magnesium silicate, alumina, aluminum oxide, hydroxylapatite, porous glass powder, ceramic particles, diatomaceous earth, starch, modified starch, agarose, polyacrylamide gel, cellulose, derivatized cellulose, chitosan or mixtures thereof. In another preferred embodiment, the adsorbent material is a heat treated silica gel.

According to another aspect of the invention, there is provided a preparative-scale sorption-driven chromatographic element including a porous tip having the shape of a cone with a vertex end having a first diameter and a base having a second diameter that is larger than the first diameter, and an elongated body of a chromatographic self-supporting adsorbent material having a first end and a second end, wherein the first end is connected to the base of the cone. In another preferred embodiment, the elongated body has a diameter the same as the second diameter where the base and the elongated body are connected, and a larger third diameter at the second end. In one embodiment, the elongated body has a diameter the same as the second diameter where the base and the elongated body are connected, and a diameter the same as the second diameter at the second end. In one embodiment of the chromatographic element, the porous tip is integrally connected to the elongated body whereas in another embodiment the porous tip is releasably connected to the elongated body. In a preferred embodiment, the adsorbent material is silica gel, magnesium silicate, alumina, aluminum oxide, hydroxylapatite, porous glass powder, ceramic particles, diatomaceous earth, starch, modified starch, agarose, polyacrylamide gel, cellulose, derivatized cellulose, chitosan or mixtures thereof. In another preferred embodiment, the adsorbent material is a heat treated silica gel.

According to another aspect of the invention, there is provided a method of chromatographic separation of an organic compound using a self-supporting chromatographic element that is made of adsorbent material with no external support formed into an elongated shape having a first end and a second end, with a focusing zone proximate to the first end and a resolution zone that extends from the focusing zone to the second end, wherein the focusing zone tapers from a small cross section at the first end to a larger second cross section where the focusing zone meets the resolution zone, and wherein the resolution zone has a cross section that is at least as large as the second cross section, the method comprising the steps of contacting a sample containing an organic compound with the first end of the element, then contacting a solvent with the first end of the element; allowing the solvent to be absorbed into the adsorbent material by capillary action, thereby causing the organic compound to move through the focusing zone into the resolution zone and concentrating the organic compound into a discrete band in the resolution zone as the organic compound moves from the small first cross section to the larger second cross section. In one embodiment of the method, contacting a sample is performed by placing the first end of the element into a chemical reaction chamber. In another embodiment, contacting a sample is performed by contacting the first end of the element to an adsorbent material containing the sample. Another embodiment further includes the steps of identifying a band of a chromatographically separated compound in the adsorbent material, excising the band by cutting out a section of the element and extracting the compound from the excised material. In one embodiment, the identifying step includes detecting a visible band in full spectrum light, detecting fluorescence of the band when exposed to ultraviolet radiation, detecting quenching of fluorescence by the band when exposed to ultraviolet radiation, enzymatically detecting the band, or detecting chemical staining of the band. In another embodiment of the method, at least one step is performed automatically.

According to another aspect of the invention there is provided a method of chromatographic separation of organic compounds using a chromatographic element including a porous tip having the shape of a cone with a vertex end having a first diameter and a base having a second diameter that is larger than the first diameter, and an elongated body of a chromatographic self-supporting adsorbent material having a first end and a second end, wherein the first end is connected to the base of the cone, the method comprising the steps of contacting the vertex with a sample containing an organic compound; contacting the vertex with a solvent; allowing the solvent to be absorbed into the adsorbent material by capillary action, thereby separating and concentrating the organic compound when the organic compound moves through the adsorbent material from the first diameter of the vertex to the second diameter of the cylinder. In one embodiment, contacting a sample is performed by placing the vertex into a chemical reaction chamber containing the sample. In another embodiment, contacting a sample is performed by contacting the vertex with an adsorbent material containing the sample. In another embodiment, a sample applied to the vertex is focused by solvent-mediated capillary movement through the porous tip from the vertex into the adsorbent material of the elongated body. Another embodiment further includes the steps of identifying a band of a chromatographically separated compound in the adsorbent material, excising the band by cutting out a section of the element and extracting the compound from the excised material. In one embodiment, the identifying step includes detecting a visible band in full spectrum light, detecting fluorescence of the band when exposed to ultraviolet radiation, detecting quenching of fluorescence by the band when exposed to ultraviolet radiation, enzymatically detecting the band, or detecting chemical staining of the band. In another embodiment of the method, at least one step is performed automatically.

BRIEF DESCRIPTION OF THE DRAWINGS

FIG. 1 is a perspective view of the chromatographic system showing a preferred conical shape for the self-supporting chromatographic element with a conical shaped integral tip.

FIG. 2A is a cross-sectional view of the chromatographic element taken along the line 2A—2A of FIG. 1.

FIG. 2B is a cross-sectional view of the chromatographic element taken along the line 2B—2B of FIG. 1.

FIG. 2C is a cross-sectional view of the chromatographic element taken along the line 2C—2C of FIG. 1.

FIG. 3 is a perspective view of the chromatographic system showing a preferred cylindrical shape for the self-supporting chromatographic element with a conical shaped integral tip.

FIG. 4 is a perspective view of a self-supporting cylindrical chromatographic element coupled to a releasable porous tip.

FIG. 5 is an exploded view of the chromatographic element and releasable porous tip of FIG. 4.

FIG. 6 is a cross-sectional view of the chromatographic element and releasable porous tip taken along the line 6—6 of FIG. 5.

DETAILED DESCRIPTION OF THE INVENTION

The present invention is a chromatographic system for preparative scale isolation and purification of compounds in a mixture, particularly for purifying relatively small synthetic organic compounds. The chromatographic system of this invention is useful for preparative separation of compounds, particularly organic compounds. The compounds separate into bands by their different $R_f$ and the bands are sharpened and narrowed by passing them through a focusing zone of the element. The focusing zone extends from the vertex of the tip through portions of the tip having progressively larger cross-sectional areas. The bands then pass through the resolution zone that extends from the bottom end to the top end of the elongated body of the element, which may also have progressively larger cross-sectional areas from the bottom end to the top end. The present invention includes a useful method for preparative chromatographic separation of multiple compounds in a sample, particularly for structurally related organic compounds such as those synthesized in combinatorial syntheses. The system and method are suitable for partial or complete automation.

The system includes a self-supporting chromatographic element that has an elongated body and a porous tip. "Self-supporting" means that essentially all of the chromatographic element is capable of maintaining its shape without external support such as support walls. That is, unlike most prior art chromatographic columns, the chromatographic element of the present invention is made of relatively rigid chromatographic material that maintains its shape without any surrounding walls or tube, although it will be understood that during use the chromatographic element may be held in position by a support element (e.g., a clamp). The porous tip, which serves as a focusing zone during chromatographic separation, may be integral with or a releasably attached to the elongated body of the chromatographic element, which serves as the resolution zone during chromatography. The porous tip may be any of a variety of shapes having an vertex and a wider portion, such as solid cone, hemisphere, paraboloid or pyramid. Similarly, the elongated body of the chromatographic element may be of a variety of shapes such as a solid cylinder, cone pyramid or rectangular box.

The system may also include a porous solvent transfer block for providing solvent to the chromatographic element. The solvent transfer block may be of a variety of shapes such as a solid cylinder, hemisphere, cone, pyramid or box. Some preferred embodiments of the chromatographic system and the chromatographic element are illustrated in FIGS. 1–6.

Referring to FIG. 1, the chromatographic system comprises a chromatographic element 10 with a top end 12 and a bottom end 14 and an elongated body 16 therebetween. In this embodiment, the bottom end 14 of the elongated body 16 of the element is integrally attached to a porous tip 18. The tip 18 terminates in a vertex 20 for receiving a sample and solvent used to chromatographically resolve the compounds contained in the sample. The vertex 20 is preferably an elliptical shaped point. The elongated body 16 of the chromatographic element and the tip 18 may be made of the same self-supporting chromatographic medium 22 or the body and the tip may be made of different materials. In the embodiment shown in FIG. 1, the elongated body and the tip are integrally formed of the same self-supporting chromatographic medium.

The system shown in FIG. 1 also includes a porous solvent transfer block 24 for receiving solvent 34 from a source and transferring it to the chromatographic element 10. The solvent transfer block has a top end 26, a bottom end 28 and walls 30 extending therebetween. As shown, the top end 26 defines a first plane, the bottom end 28 defines a second plane, with the two planes parallel to each other and the walls 30 orthogonal to the planes. To efficiently transfer solvent to the chromatographic element 10, the top end 26 of the solvent transfer block 24 preferably has a depression 32 which is sized and shaped to receive the vertex 20 of the tip 18. Although FIG. 1 shows the solvent transfer block 24 as a solid cylinder, any of a variety of shapes may be used such as a solid box, hemisphere, pyramid or cone.

The chromatographic element 10 shown in FIG. 1 has a cone shaped tip 18 integrally attached to the bottom end 14 of an elongated body 16 that is substantially a flattened cone shape. That is, the elongated body 16 has a smaller diameter at the bottom end 14 and a wider diameter at the top end 12. As shown in FIGS. 2A–2C, the chromatographic element is made of a self-supporting chromatographic medium 22 and has progressively increasing diameters progressing from the vertex 20 through the tip portion (shown in FIG. 2A) to the middle of the body of the element (shown in FIG. 2B) to the upper portion of the body of the element (shown in FIG. 2C).

FIG. 3 illustrates another embodiment of the chromatographic system similar to that shown in FIG. 1 but using a chromatographic element 10 having a solid cylindrical shaped elongated body 16 integrally attached to the porous tip 18. Both the body and tip of the chromatographic element are of the same self-supporting chromatographic medium 22. The tip 18 terminates in a vertex 20 for receiving a sample and solvent, shown inserted into a depression 32 on the top 26 of a porous solvent transfer block 24 as described for FIG. 1.

Another embodiment of a chromatographic element 10 is illustrated in FIG. 4. This chromatographic element has two releasably attached portions: the elongated body 16 of the chromatographic element and a porous tip, shown with the body of the element inserted into the porous tip 18. Because these two portions can be separated from each other, different combinations of materials can be used in the body of the element and in the tip. That is, the elongated body 16 of the element may be made of one chromatographic medium whereas the porous tip 18 can be made of another chromatographic medium or of a nonadsorbent porous material such as a fritted material. Moreover, because the two components of the chromatographic element are separable, the tip may be used repeatedly in combination with any of a variety of elongated bodies made of any suitable chromatographic medium for the particular compounds to be separated. The choice of materials used in any combination of elongated body and tip will be determined by the user based on the compounds to be separated and well known physical properties of the materials (e.g., sieve size of a chromatographic medium or solubility of the material in a solvent).

FIG. 5 shows the chromatographic element 10 as shown in FIG. 4, but with the elongated body 16 of the element separated from the porous tip 18. FIG. 6 is a cross-sectional view of the separated chromatographic element of FIG. 5. Referring to FIGS. 5 and 6, the elongated body 16 is made of a self-supporting chromatographic medium 22. The porous tip 18 has an vertex 20, an upper portion 36 opposite the vertex and a lower portion 38 terminating in the vertex 20. The upper portion 36 of the tip 18 includes walls 40 sized to receive and hold the bottom 14 of the elongated body 16 of the element 10. Although the walls 40 are shown only in the upper portion of the tip in FIGS. 5 and 6, it will be understood that the walls may extend over some of the lower portion 38 of the tip, such as a tubular sleeve around a portion of the tip and extending upward to receive the bottom end of the elongated body of the element. The lower portion 38 of the tip 18 includes a porous material 42 such as glass beads, sand or a fritted material. Preferably the porous material 42 is a self-supporting material such as sintered glass or sintered steel. The porous material 42 may be used to integrally form the walls 40 of the tip or the walls may be made of a nonporous material. A somewhat pliable and expandable nonporous material may provide a relatively tight frictional connection to the body of the element when the bottom of the elongated body is inserted into the tip. For example, the tip may include a solid conical lower portion 38 made of a porous fritted material and walls made of a tubular polytetrafluoroethylene (PTFE, TEFLON®) sleeve fitted around the conical lower portion and extending upward to hold the bottom of the elongated body adjacent to the porous tip.

The tip 18 may also include a septum 44 adjacent to the porous material 42 and contained within the walls 40 of the tip 18. In this embodiment, the septum 44 and the walls 40 of the tip form a receptacle 46 for the bottom 14 of the elongated body 16. When the elongated body 16 of the element 10 is inserted into the receptacle 46, the septum 44 serves as an interface between the porous material 42 and chromatographic medium 22 of the element 10. The septum is preferably capable of holding a particulate porous material 42 in place within the tip and is made of a nonswellable porous matrix such as a semipermeable polymeric film or plug, or a fibrous matrix of glass wool.

The porous tip is preferably made of a self-supporting material such as the same chromatographic medium used in the elongated body of the chromatographic element, and may be integrally formed of the same material as used to form the elongated body of the element (e.g., as shown in FIGS. 1 and 3). Alternatively (as shown in FIG. 6), the porous tip may be made of a self-supporting porous material different from that of the adsorbent chromatographic medium such as fritted or sintered glass, sintered steel, porous fibrous polymeric material such as PTFE or nylon, porous ceramic, or a gel such as an agarose or polyacrylamide gel. Preferably, the porous tip, when not made of the chromatographic medium, is made of sintered glass which can be made from powdered soda lime glass, borosilicate glass, high silicate glass, crystallized glass or lead silicate glass having an average particle size of about $1\mu$ to $50\mu$ in the largest dimension. A sintered steel having an average pore size of about $1\mu$ to about $50\mu$ is also appropriate.

A wide variety of chromatographic media are known and may be used to form a self-supporting chromatographic element. Suitable chromatographic solid phase materials are, for example, activated charcoal (e.g., carbosieve), silica gel, magnesium silicate, alumina, aluminum oxide, hydroxylapatite, porous glass powder, ceramic particles, diatomaceous earth, starch, modified starch, agarose, polyacrylamide gel, cellulose, derivatized cellulose, chitosan or mixtures thereof contained in self-supporting formulations. Self-supporting formulations may include binders with the adsorbent material such as gypsum, carboxymethyl cellulose or starch. The chromatographic medium may also include a fluorescent indicator such as zinc silicate. The particulate solid phase adsorbent material may be contained within a fibrous inert matrix such as described in U.S. Pat. No. 4,906,378. The preferred chromatographic medium is capable of withstanding chromatographic temperatures and fluid conditions without dissolving, disintegrating or softening significantly. Also, the chromatographic medium is preferably relatively transparent to allow visual detection of the solvent front and separated compounds in the adsorbent material. Most preferably, the chromatographic medium is transparent to ultraviolet (UV) radiation such that separated compounds within the medium can be detected upon exposure of the chromatographic element to UV radiation (either by detecting fluorescence or quenching of fluorescence in the medium). Preferred chromatographic media are silica gel and aluminum oxide, both formulated with a binder that is preferably carboxymethyl cellulose, starch or gypsum.

The elongated body of the chromatographic element can be any of a variety of shapes such as cylinders, cones, pyramids, rectangular boxes and preferably is cylindrical or conical as shown in FIGS. 1 and 3–6. The tip of the element preferably has a base of similar size and shape as that of the bottom end of the elongated body of the element and terminates in an vertex for receiving sample and solvent. A conical shaped tip with an elliptical vertex is preferred. The largest cross-sectional dimension of the elongated body of a chromatographic element is about 0.5 cm to about 100 cm, preferably about 1 cm to about 75 cm, and most preferably about 1 cm to about 40 cm. The length of the elongated body of the chromatographic element is about 1 cm to about 1,000 cm, preferably about 3 cm to about 500 cm, and most preferably about 5 cm to about 250 cm. The porous tip preferably has the capacity to hold volumes of about 5 $\mu$l to about 50 ml, preferably about 50 $\mu$l to about 30 ml, and most preferably about 100 $\mu$l to about 20 ml.

The general method of using the above-described chromatographic element and system for purifying a compound from a mixture includes the steps of contacting the vertex of the tip with a sample containing one or more organic compounds of interest whereby the sample is taken up into the tip, then contacting the vertex with a solvent and allowing the solvent to be absorbed via the tip into the adsorbent material by capillary action. The tip, having a relatively small diameter, serves as a focusing zone for the sample as it moves through the tip and into the larger diameter of the elongated body of the chromatographic element which serves as the resolving zone. As compounds move through the chromatographic medium with the solvent, they separate and the configuration of the element can concentrate the compounds into narrow bands as they move through the adsorbent material from a first smaller diameter of the vertex to a second larger diameter of the chromatographic element. Although the compounds move at their respective $R_f$ through the chromatographic medium, it will be appreciated that the bands will further be sharpened and narrowed if the elongated body of the element also has a first narrower diameter at the bottom end and a second wider diameter at the top end of the elongated body.

The vertex contacts the sample, for example, by placing the vertex of the tip into the sample. The sample may be presented in any of a variety of forms such as a liquid in a reaction chamber, a droplet placed on a nonadsorbent surface, a sample-saturated material, or a liquid dispensed to the vertex (where the dispensing rate is less than or equal to the rate that the sample is taken up by the porous tip) and the like.

The vertex may similarly contact the solvent in a container or via a dispensing mechanism. Preferably the vertex contacts a solvent transfer block, most preferably by placing the tip in a depression in the solvent transfer block where the depression is sized to loosely fit the vertex of the tip. The vertex is allowed to contact the solvent transfer block for sufficient time to allow the chromatographic medium to be in fluid contact with the solvent thereby transferring solvent via capillary action from the block to the chromatographic medium to separate the compounds in the mixture by adsorption. Because the solvent is substantially contained within the porous block and because solvent transfer from the block to the tip is efficient, solvent wastage is minimized and exposure of personnel to solvent in liquid or vapor form is also decreased relative to the use of conventional solvent trays.

The chromatographic element is allowed to continue to take up solvent until the solvent front and/or a band of interest has moved sufficiently along the chromatographic medium to permit separation of the compound from others in the mixture. The solvent front and/or band of interest may be detected visually or spectrophotometrically using any of a variety of band signals, such as colored bands in visible spectrum light, fluorescent bands upon exposure to UV radiation or quenching of a fluorescent marker in the chromatographic medium where the compound of interest is located.

Once a band of interest is detected and located at an appropriately separated position, the solvent flow is terminated by removing the chromatographic element from the source of solvent. Then the band of interest is directly excised from the chromatographic element, for example, by cutting the chromatographic material above and below the band and excising the band-containing material. Then the compound of interest is eluted from the band-containing material using well known elution methods. For example, the excised chromatographic material may be broken up or crushed to increase solvent contact with the material, and the material suspended in the appropriate solvent to elute the compound by agitating or percolating solvent through the medium. The eluates containing the compound of interest may then be concentrated by any of a variety of well known techniques such as evaporation or lyophilization.

It will be appreciated that all or some of the steps in the method can be automated, preferably with complete automation of the process from sample application through purification of the compound of interest. For example, the chromatographic element of the system may be robotically controlled so that it is sequentially brought into contact with the sample and solvent and then removed from the solvent for detection and isolation of the band of interest. Dispensing of samples and/or solvent is also suitable for automation using, for example, an automatic pipetting system for dispensing sample to the tip and appropriate amounts of the solvent to the solvent transfer block at the appropriate times. Automatic spectrophotometric detection of the solvent front or compound band(s) of interest (either by light absorbance or fluorescence) using well known methods is preferred. For example, a compound that serves as an internal standard may be incorporated into the sample and chromatographic progress of the standard through the element may be spectrophotometrically monitored so that the element is automatically removed from contact with the solvent when the standard reaches a predetermined location in the chromatographic element. Then, the chromatographic element may be scanned spectrophotometrically for the presence of compound band(s) of interest which are then automatically cut out of the element and eluted in individual elution chambers. The eluates can then be automatically scanned or sampled for detection of the compound of interest and the compound-containing eluates can be pooled for concentration of the purified compound.

The chromatographic elements are 1 cm to 200 cm in length, preferably 3 cm to 50 cm in length, and most preferably 5 to 25 cm in length. The diameters of the chromatographic elements are 0.1 mm to 50 cm, preferably 0.1 mm to 10 cm and most preferably 0.1 mm to 1 cm. Such elements can be used to separate compounds in samples of 0.01 ml to 100 ml, or preferably in samples of 0.1 ml to 10 ml. The adsorbent materials used to make the chromatographic elements include activated charcoal, silica gel, magnesium silicate, alumina, aluminum oxide, hydroxylapatite, porous glass powder, ceramic particles, diatomaceous earth, starch, modified starch, agarose, polyacrylamide gel, cellulose, derivatized cellulose, chitosan or mixtures thereof that are formed into self-supporting elements. The adsorbent material may contain binders such as calcium sulfate, sodium silicate, starch or modified starch, or carboxymethyl cellulose to assist in forming the adsorbent material into the self-supporting element. Preferred adsorbent materials are silica gel, silica gel containing calcium sulfate as a binder, alumina, magnesium silicate, microcrystalline silicate, carboxymethyl cellulose, modified starch (esters or ethers) and silica modified as for use in reverse phase chromatography. It will be understood that additional components to aid in identifying the compounds within the adsorbent material may also be included, such as zinc sulfate as a fluorescent indicator. Another preferred form of the chromatographic element is made of polyacrylamide gel of a sufficient percentage to allow the element to be self-supporting (e.g., 10 to 20%) to which electrodes of different polarity may be attached at the two ends of the element such that the element can be used for electrophoretic separation of compounds within the element using standard electrophoresis techniques.

In general the chromatographic element is made by mixing an adsorbent material with a binder (if the adsorbent material is not self-binding) in a aqueous slurry or paste which is poured into a mold of appropriate size and dimensions. For example, silica gel mixed with calcium sulfate binder and water to form a paste may be used with a mold made of any nonadherent material such as a plastic polymer, e.g., PTFE. The paste is allowed to set from 20 min to about 1 week and then the molded element is removed from the mold. The molded element is allowed to completely dry by air drying at ambient temperature, usually from 8 hr to 1 week, or by placing it in an oven to dry at elevated temperature. The element can be dried in the oven at 50° C. to 500° C. for about 8 hr to 1 week depending on the adsorbent material and binder used and the dimensions of the element. For example, an element made using an organic binder such as starch is generally dried at about 50° to 60° C. whereas an element made of a self-binding alumina gel can be dried at 250° C. to 500° C.

Unless defined otherwise, all scientific and technical terms used herein have the same meaning as commonly understood by those skilled in the relevant art. Unless mentioned otherwise, the techniques employed or contemplated herein are standard methodologies well known to one of ordinary skill in the art. The following examples of embodiments are for illustration only and are not to be construed as limiting the scope of the invention.

EXAMPLE 1

A Chromatographic Element with an Integral Tip

The chromatographic element is made of silica gel containing 35% calcium sulfate by weight. The element has a conical elongated body having a diameter of 1 cm at the top end and a diameter of 0.5 cm at the bottom end of the elongated body, and an elongated body of 10 cm with the bottom end connected integrally to a conical tip having an elliptical vertex. The tip has a base of the same diameter as the bottom end of the elongated body (0.5 cm), a cone height of 1 cm and terminates in an elliptical vertex of 0.01 mm. The element is formed by pouring an aqueous slurry or paste of the silica gel into a plastic mold having inner dimensions described above (i.e., the elongated body and the tip are integrally formed). The gel is allowed to set for 20 min at about 25° C. and is then heat dried at 250° C. for 5 to 8 hr. When the element has cooled to room temperature, the element is removed from the mold.

EXAMPLE 2

A Chromatographic Element with a Releasably Attachable Tip

The chromatographic element has an elongated body made of alumina with 20% by weight carboxymethyl cellulose binder. The elongated body of the element is a cylinder having a diameter of 2.5 cm and a length of 20 cm. The tip is a solid conical shape as illustrated in FIG. 6 made of sintered glass having an average pore size of 30$\mu$. The tip has a maximal diameter of 2.5 cm and a height of 1.5 cm with a PTFE sleeve of 1 cm surrounding the portion of the tip near the maximal diameter. The conical tip portion is slipped into the PTFE sleeve which is the fitted over one end of the elongated body of the element to form a chromatographic element such as illustrated in FIG. 4.

EXAMPLE 3

A Chromatographic System for Separation of Small Organic Compounds

The chromatographic system comprises a chromatographic element made essentially as described in Example 1. The chromatographic element is attached at its top end to a clamp connected to a motor which allows the element to be moved vertically and horizontally. The system further includes a solvent transfer block that is a solid cylinder having a diameter of 1.5 cm and a height of 1.5 cm, made of sintered glass having an average pore size of 50$\mu$. The top face of the solvent transfer block has a depression about 1 to 3 mm deep and about 2 mm in diameter for receiving the vertex of the porous tip of the chromatographic element. The solvent transfer block is placed in a shallow tray containing solvent to allows efficient transfer of the solvent to the element.

EXAMPLE 4

Chromatographic Separation of Small Organic Compounds in a Mixture

The chromatographic element is made essentially as described in Example 1 but also containing zinc silicate as a fluorescent indicator, and attached to a clamp and robotic system essentially as described in Example 3. The element is used to separate a 1:1 mixture of naphthalene and 2-methoxynaphthalene (30 mg each dissolved in 2 ml of hexane).

The chromatographic element is first dipped into a well containing the 2 ml naphthalene and 2-methoxynaphthalene mixture. When all of the sample has been adsorbed into the element, the chromatographic element is robotically moved to a solvent transfer block essentially as described in Example 3 which is placed in a tray or dish containing about 10 ml of hexane. The vertex tip of the element is placed into the depression so that the tip contacts the solvent transfer block and the entire apparatus is enclosed in a covered developing chamber to contain solvent vapor. When the hexane has reached the top of the element as detected by visual inspection, the chromatographic element is removed from contact with the solvent transfer block by raising the tip out of the depression. The chromatographic element is then placed on an aluminum foil surface and exposed to UV light to cause the bands to be visualized. The positions of the bands are marked by marking the element with a pencil and under normal light the element is cut with a knife blade to release the portions containing the naphthalene and 2-methoxynaphthalene bands. The excised sections are individually placed in a fritted funnel, crushed with a glass rod and the compounds are extracted with a 1:1 mixture of hexane and ether. The eluates are dried on a rotary evaporator device using standard methods. The purity of the separated compounds is determined using standard methods such as thin layer chromatography with hexane as the developing agent or by nuclear magnetic resonance analysis.

It should be apparent from the foregoing description that various other agents may be substituted in the examples to give similar results. Accordingly, the invention may be embodied in other specific forms without departing from it in spirit to be considered in all respects only as illustrative and not as restrictive, and the scope of the invention is, therefore, indicated by the appended claims rather than by the foregoing description. All modifications which come within the meaning and range of the lawful equivalency of the claims are to be embraced within their scope.

What is claimed is:

1. A preparative-scale sorption-driven chromatographic system, comprising a self-supporting chromatographic element, said chromatographic element being adsorbent material with no external support formed into an elongated shape having a first end and a second end, with a focusing zone proximate to said first end and a resolution zone that extends from said focusing zone to said second end, wherein said focusing zone tapers from a small cross section at said first end to a larger second cross section where said focusing zone meets said resolution zone, and wherein said resolution zone has a cross section that is at least as large as the second cross section.

2. The chromatographic system of claim 1, wherein the first end includes a sample application zone proximal to the focusing zone and distal to the resolution zone.

3. The chromatographic system of claim 1, wherein the focusing zone has the shape of essentially a solid cone, hemisphere, paraboloid or pyramid.

4. The chromatographic system of claim 1, wherein the resolution zone has a uniform circular cross-section.

5. The chromatographic system of claim 1, wherein the resolution zone has a circular cross section that progressively increases in cross section from the second cross section where said focusing zone meets said resolution zone to a larger cross section at said second end.

6. The chromatographic system of claim 1, wherein the elongated shape is a cylinder, cone, pyramid or rectangular box.

7. The chromatographic system of claim 1, wherein said focusing zone and said resolution zone are integrally connected.

8. The chromatographic system of claim 1, wherein said focusing zone and said resolution zone are releasably attachable separate zones.

9. The chromatographic system of claim 1, further comprising a porous solvent transfer block.

10. The chromatographic system of claim 9, wherein said solvent transfer block is a fritted material having a depression for receiving said first end of said chromatographic element.

11. A preparative-scale sorption-driven chromatographic element, comprising a porous tip having the shape of a cone with a vertex end having a first diameter and a base having a second diameter larger than said first diameter, and an elongated body of a chromatographic self-supporting adsorbent material having a first end and a second end, wherein said first end is connected to said base of said cone.

12. The chromatographic element of claim 11, wherein said elongated body has a diameter the same as the second diameter where said base and said elongated body are connected, and a larger third diameter at said second end.

13. The chromatographic element of claim 11, wherein said elongated body has a diameter the same as the second diameter where said base and said elongated body are connected, and a diameter the same as the second diameter at said second end.

14. The chromatographic element of claim 11, wherein said porous tip is integrally connected to said elongated body.

15. The chromatographic element of claim 11, wherein said porous tip is releasably connected to said elongated body.

16. The chromatographic element of claim 1 or 11, wherein the adsorbent material is silica gel, magnesium silicate, alumina, aluminum oxide, hydroxylapatite, porous glass powder, ceramic particles, diatomaceous earth, starch, modified starch, agarose, polyacrylamide gel, cellulose, derivatized cellulose, chitosan or mixtures thereof.

17. The chromatographic element of claim 16, wherein said adsorbent material is a heat treated silica gel.

18. A method of chromatographic separation of an organic compound using a self-supporting chromatographic element that is made of adsorbent material, with no external support, formed into an elongated shape having a first end and a second end, with a focusing zone proximate to the first end and a resolution zone that extends from the focusing zone to the second end, wherein the focusing zone tapers from a small cross section at the first end to a larger second cross section where the focusing zone meets the resolution zone, and wherein the resolution zone has a cross section that is at least as large as the second cross section, comprising the steps of:

contacting a sample containing an organic compound with the first end of the element;

then contacting a solvent with the first end of the element;

allowing said solvent to be absorbed into said adsorbent material by capillary action, thereby causing said organic compound to move through said focusing zone into said resolution zone and concentrating said organic compound into a discrete band as said organic compound moves from the small first cross section of said focusing zone to the larger second cross section of said focusing zone.

19. The method of claim 18, wherein contacting a sample is performed by placing the first end of the element into a chemical reaction chamber.

20. The method of claim 18, wherein contacting a sample is performed by contacting the first end of the element to an adsorbent material containing the sample.

21. A method of chromatographic separation of organic compounds using a chromatographic element including a porous tip having the shape of a cone with a vertex end having a first diameter and a base having a second diameter larger than said first diameter, and an elongated body of a chromatographic self-supporting adsorbent material having a first end and a second end, wherein said first end is connected to said base of said cone, the method comprising the steps of:

contacting said vertex with a sample containing an organic compound;

contacting said vertex with a solvent;

allowing said solvent to be absorbed into said adsorbent material by capillary action, thereby separating and concentrating said organic compound when said organic compound moves through the adsorbent material from the first diameter of said vertex to the second diameter of said base and into said first end of said elongated body.

22. The method of claim 21, wherein contacting a sample is performed by placing the vertex into a chemical reaction chamber containing the sample.

23. The method of claim 21, wherein contacting a sample is performed by contacting the vertex with an adsorbent material containing the sample.

24. The method of claim 18 or 21, further comprising the steps of identifying a band of a chromatographically separated compound in said adsorbent material, excising said band by cutting out a section of said element and extracting said compound from said excised material.

25. The method of claim 24, wherein the identifying step comprises detecting a visible band in full spectrum light, detecting fluorescence of the band when exposed to ultraviolet radiation, detecting quenching of fluorescence by the band when exposed to ultraviolet radiation, enzymatically detecting the band, or detecting chemical staining of the band.

26. The method of claim 25, wherein at least one step is performed automatically.

* * * * *